United States Patent
Heck

(10) Patent No.: US 8,185,997 B2
(45) Date of Patent: May 29, 2012

(54) METHOD AND APPARATUS FOR CLEANING THE INTERIOR CANNULA OF LAPAROSCOPIC AND ENDOSCOPIC ACCESS DEVICES

(75) Inventor: Sandy Heck, Forest Hills, NY (US)

(73) Assignee: New Wave Surgical Corporation, Coral Springs, FL (US)

( * ) Notice: Subject to any disclaimer, the term of this patent is extended or adjusted under 35 U.S.C. 154(b) by 786 days.

(21) Appl. No.: 12/261,183

(22) Filed: Oct. 30, 2008

(65) Prior Publication Data
US 2009/0113644 A1 May 7, 2009

Related U.S. Application Data

(60) Provisional application No. 60/985,359, filed on Nov. 5, 2007.

(51) Int. Cl.
*B08B 9/00* (2006.01)

(52) U.S. Cl. ............ 15/104.16; 15/118; 604/1; 604/362

(58) Field of Classification Search ............... 15/104.05, 15/104.16–104.2, 118, 244.1; 604/1, 362
See application file for complete search history.

(56) References Cited

U.S. PATENT DOCUMENTS

| | | | | |
|---|---|---|---|---|
| 2,294,186 | A * | 8/1942 | Kirschbaum | 604/1 |
| 3,376,867 | A * | 4/1968 | Kanbar et al. | 604/1 |
| 3,566,871 | A * | 3/1971 | Richter et al. | 604/362 |
| 3,586,380 | A * | 6/1971 | Alibeckoff | 300/21 |
| 3,736,935 | A * | 6/1973 | Reimels | 604/362 |
| 3,977,406 | A * | 8/1976 | Roth | 604/362 |
| 4,114,601 | A * | 9/1978 | Abels | 600/20 |
| 4,639,253 | A * | 1/1987 | Dyer et al. | 604/362 |
| 4,887,994 | A * | 12/1989 | Bedford | 604/1 |
| 5,407,423 | A * | 4/1995 | Yoon | 604/1 |
| 6,045,623 | A * | 4/2000 | Cannon | 134/8 |
| 6,276,018 | B1 * | 8/2001 | Leiman et al. | 15/104.19 |
| 2005/0049563 | A1 * | 3/2005 | Fabian | 604/362 |
| 2005/0267395 | A1 * | 12/2005 | Mangold et al. | 604/1 |
| 2009/0118586 | A1 * | 5/2009 | Griffin | 600/204 |
| 2010/0139018 | A1 * | 6/2010 | Maslanka | 15/104.05 |

* cited by examiner

*Primary Examiner* — Mark Spisich
(74) *Attorney, Agent, or Firm* — McCormick, Paulding & Huber LLP

(57) ABSTRACT

A trocar cleaning device includes a connecting rod having a first end and a second end. A first sponge is coupled to the first end of the connecting rod, and a second sponge is coupled to the second end of the connecting rod. An X-ray detectable element is coupled to at least one of the connecting rod, the first sponge, and the second sponge.

27 Claims, 2 Drawing Sheets

METHOD AND APPARATUS FOR CLEANING THE INTERIOR CANNULA OF LAPAROSCOPIC AND ENDOSCOPIC ACCESS DEVICES

CROSS-REFERENCE TO RELATED APPLICATION

This application claims the benefit of U.S. Provisional Application Ser. No. 60/985,359, filed on Nov. 5, 2007, entitled "Method and Apparatus for Cleaning the Interior Cannula of Laparoscopic and Endoscopic Access Devices", the disclosure of which is hereby incorporated by reference in its entirety.

FIELD OF INVENTION

This invention generally relates to a device for cleaning surgical instruments, and more particularly relates to a surgical device and method for cleaning the internal cannula of access devices used in videoscopic medical procedures.

BACKGROUND

Access devices commonly referred to as trocars are inserted into the body by the surgeon or medical staff at the beginning of a procedure to maintain an open channel into a body cavity for the easy introduction of endoscopic cameras or other minimally invasive surgical instruments. The videoscopic procedures that use trocar access devices include laparoscopies, arthroscopies, thracoscopies, pelviscopies, and cystoscopies.

During minimally invasive surgical procedures, the endoscopic camera and all instruments must be passed through channels maintained open by access devices commonly called trocars. Because instruments are repeatedly inserted in and pulled out of these trocars over the course of a procedure, the internal cannula or walls of the trocar can accumulate blood, tissue and other bodily fluids that instruments have come into contact with inside the body cavity. This is particularly the case when specimens of tissue are intentionally removed from the body through these trocars for diagnostic or therapeutic purposes.

Surgeons currently have no devices or methods for effectively cleaning the internal walls of trocar access devices. Because cameras are passed into body cavities through these channels, surgeons and medical staff often find that their endoscopic image is blurred or blocked when the lens picks up the blood, tissue, or other debris along the trocar's wall as it is passed into the body through these channels. Once the camera is inside the body and the problem is identified, the endoscope must be removed again and cleaned. This is still no guarantee that the vision will be clear upon reinsertion, as the fluids that were coating the internal walls of the trocar may still remain.

If the surgeon believes that he or she can no longer proceed because the camera can not be inserted through the trocar without collecting an unacceptable amount of debris on the lens, the surgeon may roll up a piece of gauze or other towel and attempt to introduce it into the trocar either manually or with the aid of a grasping instrument. While this may clean the proximal end of the trocar's internal cannula, it typically fails to reach the distal end and is certainly not capable of thoroughly scrubbing the internal walls of the trocar.

It is therefore a general object of the present invention to provide a device and method of overcoming the above-mentioned drawbacks in cleaning the internal cannula or wall of trocars or similar laproscopic and endoscopic surgical access devices.

SUMMARY OF THE INVENTION

In an aspect of the present invention, a trocar cleaning device includes a connecting rod having a first end and a second end. A first sponge is coupled to the first end of the connecting rod, and a second sponge is coupled to the second end of the connecting rod. An X-ray detectable element is coupled to at least one of the connecting rod, the first sponge, and the second sponge.

BRIEF DESCRIPTION OF THE DRAWINGS

These objects and features of the invention will be more clearly understood from the following detailed description along with the accompanying drawing figures, wherein.

BRIEF DESCRIPTION OF THE PREFERRED EMBODIMENTS

Figure 1:
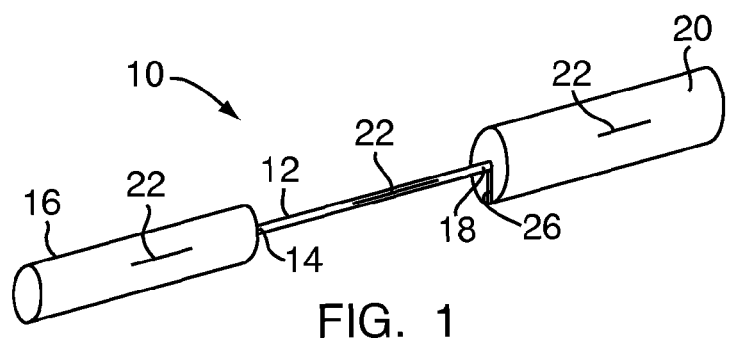
FIG. 1 is a perspective view of a trocar cleaning device including cylindrically-shaped cleaning sponges coupled at each end of a connecting rod in accordance with an embodiment of the present invention.
Figure 2A:
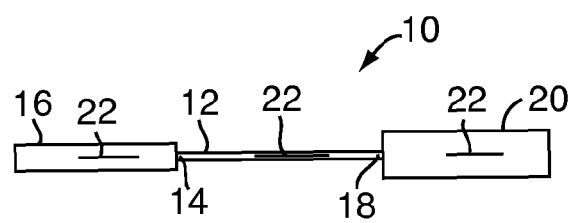
FIG. 2A is a side elevational view of the device of FIG. 1.
Figure 2B:
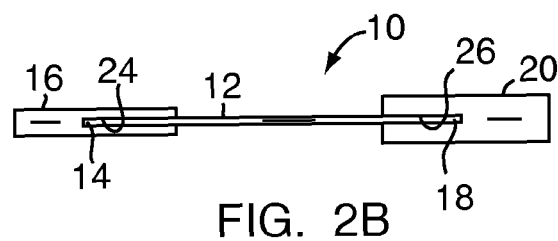
FIG. 2B is a side elevational view of the device of FIG. 1 wherein the sponges are transparent to show the connecting rod extending into the center of each sponge.

With reference to FIGS. 1, 2A and 2B, a trocar cleaning device embodying the present invention is indicated generally by the reference number 10. The device 10 includes a connecting rod 12 coupled at a first end 14 to a first sponge 16 and coupled at a second end 18 to a second sponge 20. The sponges 16, 20 are shown as generally cylindrically-shaped, but can have other practical shapes without departing from the scope of the present invention. The trocar cleaning device 10 preferably includes an X-ray detectable element 22 coupled to or imbedded in at least one of the parts of the device 10 such as the connecting rod 12, the first sponge 16 and the second sponge 20. The connecting rod 12 can be coupled to ends of the sponges 16, 20.

The X-ray detectable element 22 can include a radiopaque tape that is adhered to or otherwise coupled to the connecting rod 12 either in a circumferential or longitudinal direction along the connecting rod. Radiopaque materials by definition are opaque to various forms of radiation including X-rays. The tape itself can be made of an X-ray detectable material, or the tape may include an X-ray detectable thread embedded in the tape. The tape may also be printed with colors, designs or instructional text. Moreover, the X-ray detectable element 22 also can be an X-ray detectable thread that is adhered to or otherwise coupled along the connecting rod 12. The thread can span substantially along the entire length of the connecting rod 12, and can serve to hold the device 10 in one piece in situations where the connecting rod 12 has broken and would otherwise separate into pieces.

As shown in FIG. 2B, the connecting rod 12 can extend into the sponges 16, 20 for increased structural support of the sponges on the connecting rod. More specifically, the first sponge 16 defines a first channel 24 extending into a central portion thereof. The first channel 24 receives the first end 14 of the connecting rod 12. Likewise, the second sponge 20 defines a second channel 26 extending into a central portion thereof. The second channel 26 receives the second end 18 of the connecting rod 12. As shown in FIGS. 1, 2A and 2B, the first sponge 16 and the second sponge 20 are spaced from one another in end-to-end relationship along the connecting rod 12 so as to expose a portion of the connecting rod therebetween.

The present invention relates to a single patient use, sterile device that is comprised of a connecting rod with absorptive sponges at both ends. The sponges on each end of the connecting rod can have different average diameters relative to each other. For example, the dimensions of the first sponge 16 on one end of the connecting rod 12 are designed for cleaning an access device with an internal cannula that is about 5 mm in diameter, and the dimensions of the second sponge 20 on the other end of the connecting rod 12 are designed to clean an access device with an internal cannula that is about 10 mm in diameter. With these dimensions in mind by way of example only, at their widest points one absorptive end of the first sponge 16 has a diameter of greater than about 10 mm and that of the second sponge 20 has a diameter in the range of about 5 mm to about 10 mm. The full length of the device 10 from one end to the other is preferably greater than about 6 inches (152.4 mm).

The material of the sponges can be foam, fabric, or any other material or combination of materials that are both durable and absorptive. The absorptive ends are preferably composed of a microfiber material. This can be a piece of microfiber fabric folded, pressed or rolled onto itself, or it could be a surface of microfiber cloth over a foam, cotton or rayon core (or perhaps another absorptive material). What constitutes the microfiber is the D.P.F. or "denier per filament". The microfiber material preferably has a D.P.F. from about 0.05 to about 1.5.

The absorptive end of the sponges could be shaped as a sphere with the connecting rod intersecting its center, an ovoid shape with its long axis in line with the connecting rod, or a cone also with the long axis in line with the connecting rod and with the base at the distal end. It is important that the widest parts of the absorptive ends of the sponges are able to clean the underside of a trocar tip and the underside of a trocar valve as they are pulled from the trocar. To this end, the absorptive ends may be designed with ridges or a lip as will be later described with reference to FIGS. 8 and 9.

The material of the connecting rod can be a plastic, a metal, or any other generally rigid material that will not easily bend or break. The total length of the device (from the outwardly facing end of one sponge to the outwardly facing end of the other sponge) preferably is at least about 6 inches (152.4 mm), but may be about 12 inches (304.8 mm) or longer. The sponges may be attached to the ends of the connecting rod, or the connecting rod may continue internally through the center of each sponge for added rigidity and support. A portion of the connecting rod may be visible in the center of the device between the two sponges, or the sponges may meet in the center of the connecting rod so as to cover the entire length of the connecting rod.

The device preferably has an X-ray detectable element imbedded in the sponges, the connecting rod, or both. This is to ensure that the location of the device can be easily identified should it accidentally be passed entirely through the trocar and into a body cavity.

The device can be opened at the beginning of the surgical procedure and kept ready for surgical staff on a sterile back table, or may be opened during the surgical procedure as needed. The device is sterilized, preferably with gamma radiation, and designed for single-patient-use only.

The device is operated by holding one end of the device by hand and passing the other end through a trocar. The device may be pushed in and pulled out of the trocar as needed to clean fluids, tissues, and other debris that has collected along the circular internal wall of the trocar. The device is for single patient use, and must be disposed of at the end of each procedure, but the device may be used repeatedly over the course of a single procedure until it becomes saturated with fluids or other debris.

Figure 3A:
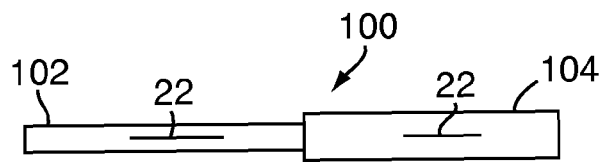
FIG. 3A is a side elevational view of a trocar cleaning device with the sponges meeting in the middle of the connecting rod such that the rod is not visible in accordance with another embodiment of the present invention.
Figure 3B:
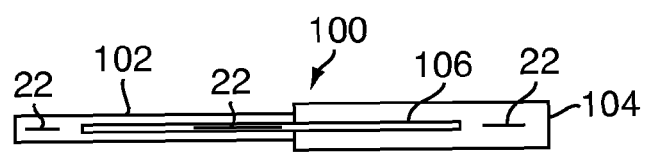
FIG. 3B is a side elevational view of the device of FIG. 3A wherein the sponges are transparent to show the connecting rod extending into the center of each sponge for structural support.

With reference to FIG. 3A, a trocar cleaning device in accordance with another embodiment is indicated generally by the reference number 100. The device 100 is generally similar to the device 10 of FIG. 1, except that ends of first and second sponges 102, 104 abut one another in end-to-end relationship along the connecting rod so as to conceal the connecting rod. With reference to FIG. 3B, the first and second sponges 102, 104 are illustrated as transparent so as to reveal an otherwise hidden connecting rod 106 extending into the first and second sponges 102, 104.

Figure 4:
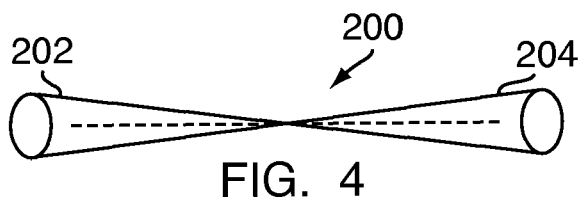
FIG. 4 is a side elevational view of a trocar cleaning device having cone-shaped sponges in accordance with another embodiment of the present invention.

With reference to FIG. 4, a trocar cleaning device 200 is generally similar to the previously illustrated devices except that first and second sponges 202, 204 are conical in shape.

Figure 5:
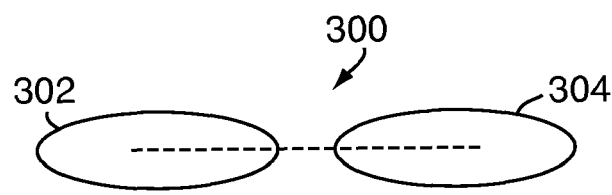
FIG. 5 is a side elevational view of a trocar cleaning device having ovoid-shaped sponges in accordance with another embodiment of the present invention.

With reference to FIG. 5, a trocar cleaning device 300 is generally similar to the previously illustrated devices except that first and second sponges 302, 304 are ovoid in shape.

Figure 6:
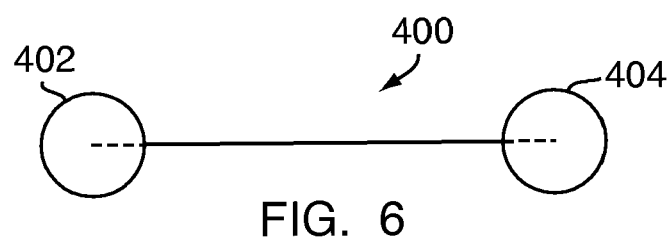
FIG. 6 is a side elevational view of a trocar cleaning device having spherically-shaped sponges in accordance with another embodiment of the present invention.

With reference to FIG. 6, a trocar cleaning device 400 is generally similar to the previously illustrated devices except that first and second sponges 402, 404 are spherical in shape.

Figure 7:
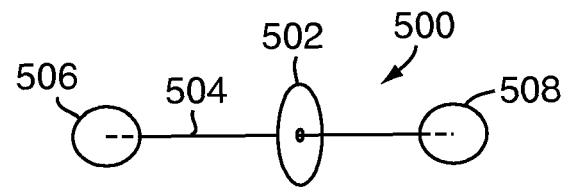
FIG. 7 is a side elevational view of a trocar cleaning device having a disk slidably coupled to the connecting rod for preventing the device from accidentally falling entirely into a body cavity.

With reference to FIG. 7, a trocar cleaning device 500 is generally similar to the previously illustrated devices except that the device further includes a disk 502 slidably coupled to a connecting rod 504 between first and second sponges 506, 508 for preventing the trocar cleaning device from accidentally passing completely through a trocar and into a body cavity of a patient undergoing a surgical procedure. The disk 502 is preferably formed of a generally rigid material such as plastic, and is sized to slide freely along the length of the exposed connecting rod but not travel over the absorptive end of the sponges 506, 508. In an exemplary embodiment, the disk is greater than about 12 mm in diameter to prevent the device from falling entirely into the body cavity. However, the disk 502 can be either smaller or larger in diameter without departing from the scope of the present invention.

Figure 8:
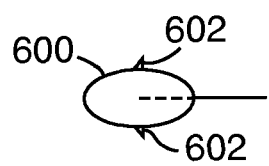
FIG. 8 is a side elevational view of a sponge having a raised lip or fin circumferentially extending thereabout to ensure cleaning of the inner wall of a trocar.
Figure 9:
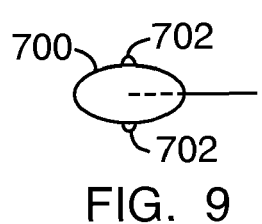
FIG. 9 is a side elevational view of a sponge having a raised rounded ridge circumferentially extending thereabout to ensure cleaning of the inner wall of a trocar.

As shown in FIGS. 8 and 9, the sponges can include an outwardly extending projection extending circumaxially about a connecting rod for pressing against an inner surface of a trocar and thereby improve the cleaning action of the sponges. The projections can take various practical shapes. As shown in FIG. 8, for example, a sponge 600 includes a circumaxially extending projection 602 having a fin-like shape. As shown in FIG. 9, for example, a sponge 700 includes a circumaxially extending projection 702 in the form of a raised rounded ridge.

As will be recognized by those of ordinary skill in the pertinent art, numerous modifications and substitutions can be made to the above-described embodiments of the present invention without departing from the scope of the invention. Accordingly, the preceding portion of this specification is to be taken in an illustrative, as opposed to a limiting sense.

What is claimed is:

1. A laproscopic trocar cleaning device comprising:
    a connecting rod having a first end and a second end;
    a first sponge coupled to the first end of the connecting rod;
    a second sponge coupled to the second end of the connecting rod, the first and second sponges being generally cylindrically-shaped and having different diameters; and
    an X-ray detectable element coupled to or imbedded in at least one of the connecting rod, the first sponge, and the second sponge;
    wherein one of the first and second sponges has a diameter greater than about 10 mm, and the other of the first and second sponges has a diameter in the range of about 5 mm to about 10 mm; and
    wherein a length from outwardly facing ends of the first sponge and the second sponge is greater than about 6 inches (152.4 mm).

2. A laproscopic trocar cleaning device as defined in claim 1, wherein:
    the first sponge defines a first channel extending into a central portion thereof, the first channel receiving the first end of the connecting rod; and
    the second sponge defines a second channel extending into a central portion thereof, the second channel receiving the second end of the connecting rod.

3. A laproscopic trocar cleaning device as defined in claim 2, wherein the first sponge and the second sponge abut one another in end-to-end relationship along the connecting rod.

4. A laproscopic trocar cleaning device as defined in claim 2, wherein the first sponge and the second sponge are spaced from one another in end-to-end relationship along the connecting rod so as to expose a portion of the connecting rod therebetween.

5. A laproscopic trocar cleaning device as defined in claim 1, wherein a length from outwardly facing ends of the first sponge and the second sponge is about 12 inches (304.8 mm) or longer.

6. A laproscopic trocar cleaning device as defined in claim 1 wherein the first sponge and the second sponge each include an absorptive material.

7. A laproscopic trocar cleaning device as defined in claim 6, wherein the absorptive material includes one of foam and fabric.

8. A laproscopic trocar cleaning device as defined in claim 6, wherein the absorptive material includes a microfiber material.

9. A laproscopic trocar cleaning device as defined in claim 8, wherein the microfiber material has one of a folded, pressed, and rolled-onto-itself configuration.

10. A laproscopic trocar cleaning device as defined in claim 8, wherein the microfiber material has a D.P.F. from about 0.05 to about 1.5.

11. A laproscopic trocar cleaning device as defined in claim 1, wherein the connecting rod, the first sponge and the second sponge are in a sterilized state.

12. A laproscopic trocar cleaning device as defined in claim 1, wherein the connecting rod, the first sponge and the second sponge are in a gamma radiation sterilized state.

13. A laproscopic trocar cleaning device as defined in claim 1, wherein the first sponge and the second sponge each include a projection extending circumaxially about the connecting rod for pressing against an inner surface of a trocar.

14. A laproscopic trocar cleaning device as defined in claim 13, wherein the projection has a fin-like shape.

15. A laproscopic trocar cleaning device as defined in claim 13, wherein the projection has a raised rounded ridge shape.

16. A laproscopic trocar cleaning device as defined in claim 1, wherein the connecting rod includes a generally rigid material.

17. A laproscopic trocar cleaning device as defined in claim 16, wherein the generally rigid material includes one of plastic and metal.

18. A laproscopic trocar cleaning device as defined in claim 1, further comprising a disk slidably coupled to the connecting rod and disposed thereon between the first sponge and the second sponge, the disk being fabricated of a generally rigid material to prevent the disk from entering a trocar and thereby preventing the first sponge, the second sponge and the connecting rod all from accidentally passing through a trocar and into a body cavity.

19. A laproscopic trocar cleaning device as defined in claim 18, wherein the generally rigid material includes plastic.

20. A laproscopic trocar cleaning device as defined in claim 18, wherein the disk has a diameter greater than about 12 mm.

21. A laproscopic trocar cleaning device as defined in claim 1, wherein the X-ray detectable element includes a radiopaque tape.

22. A laproscopic trocar cleaning device as defined in claim 21, wherein the radiopaque tape is coupled to the connecting rod in a longitudinal direction along the connecting rod.

23. A laproscopic trocar cleaning device as defined in claim 21, wherein the radiopaque tape is coupled to the connecting rod in a circumferential direction along the connecting rod.

24. A laproscopic trocar cleaning device as defined in claim 21, wherein the radiopaque tape itself is an X-ray detectable material.

25. A laproscopic trocar cleaning device as defined in claim 21, wherein the radiopaque tape includes an X-ray detectable thread embedded in the radiopaque tape.

26. A laproscopic trocar cleaning device as defined in claim 1, wherein the X-ray detectable element includes an X-ray detectable thread coupled to the connecting rod.

27. A laproscopic trocar cleaning device as defined in claim 26, wherein the X-ray detectable thread extends substantially along the length of the connecting rod.

* * * * *